United States Patent [19]

Gillings

[11] 4,209,905
[45] Jul. 1, 1980

[54] DENTURE RETENTION

[75] Inventor: Barrie R. D. Gillings, Sydney, Australia

[73] Assignee: University of Sydney, Sydney, Australia

[21] Appl. No.: 904,421

[22] Filed: May 10, 1978

[30] Foreign Application Priority Data

May 13, 1977 [AU] Australia ............................. PD0090

[51] Int. Cl.² ............................................. A61C 13/00
[52] U.S. Cl. .................................................... 433/189
[58] Field of Search .................... 32/6, DIG. 6, 10 A, 32/2, 15, 8

[56] References Cited

U.S. PATENT DOCUMENTS

| | | | |
|---|---|---|---|
| 2,149,048 | 2/1939 | Freedman | 32/2 |
| 2,543,773 | 3/1951 | Goldschmidt | 32/DIG. 6 |
| 2,555,403 | 6/1951 | Freedman | 32/2 |
| 2,709,301 | 5/1955 | Goldsmith | 32/DIG. 6 |
| 2,803,879 | 8/1957 | Cook | 32/DIG. 6 |
| 3,798,770 | 3/1974 | Mitchell | 32/DIG. 6 |

FOREIGN PATENT DOCUMENTS 2308348  4/1975  France ............................................ 32/5

Primary Examiner—Russell R. Kinsey
Assistant Examiner—Michael J. Foycik, Jr.
Attorney, Agent, or Firm—Owen, Wickersham & Erickson

[57] ABSTRACT

A method of retaining dentures in position by use of magnets. A first magnet element is mounted to a support associated with a person's jawbone, such magnet element being exposed at or above the gingival margin of the person's gum, and a second magnet element is located in the denture. The second magnet element aligns with and abuts the first magnet element when the denture is fitted to the patient. Retention is achieved by way of magnetic attraction between the first and second magnet elements, one at least of which is a magnet that exhibits a magnetic field.

18 Claims, 15 Drawing Figures

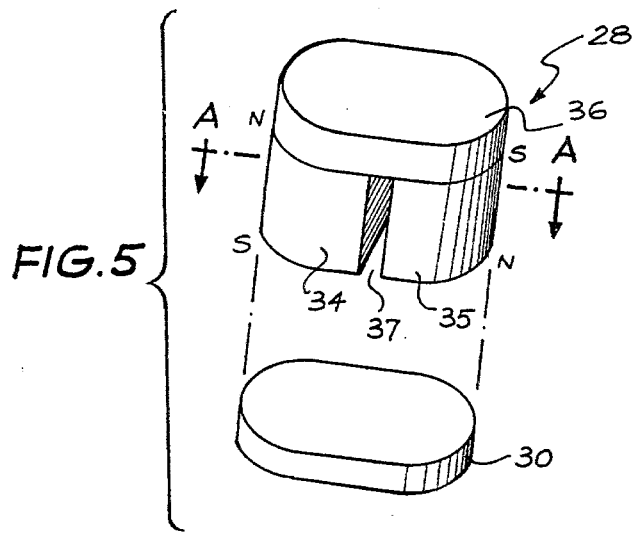
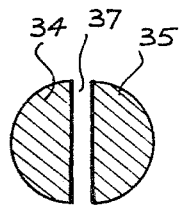
FIG. 5
FIG. 5A
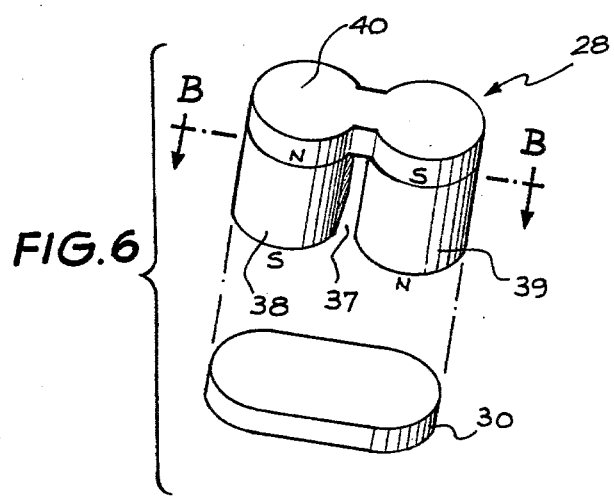
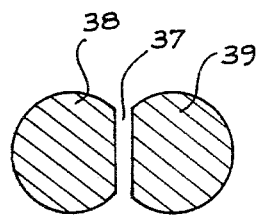
FIG. 6
FIG. 6A

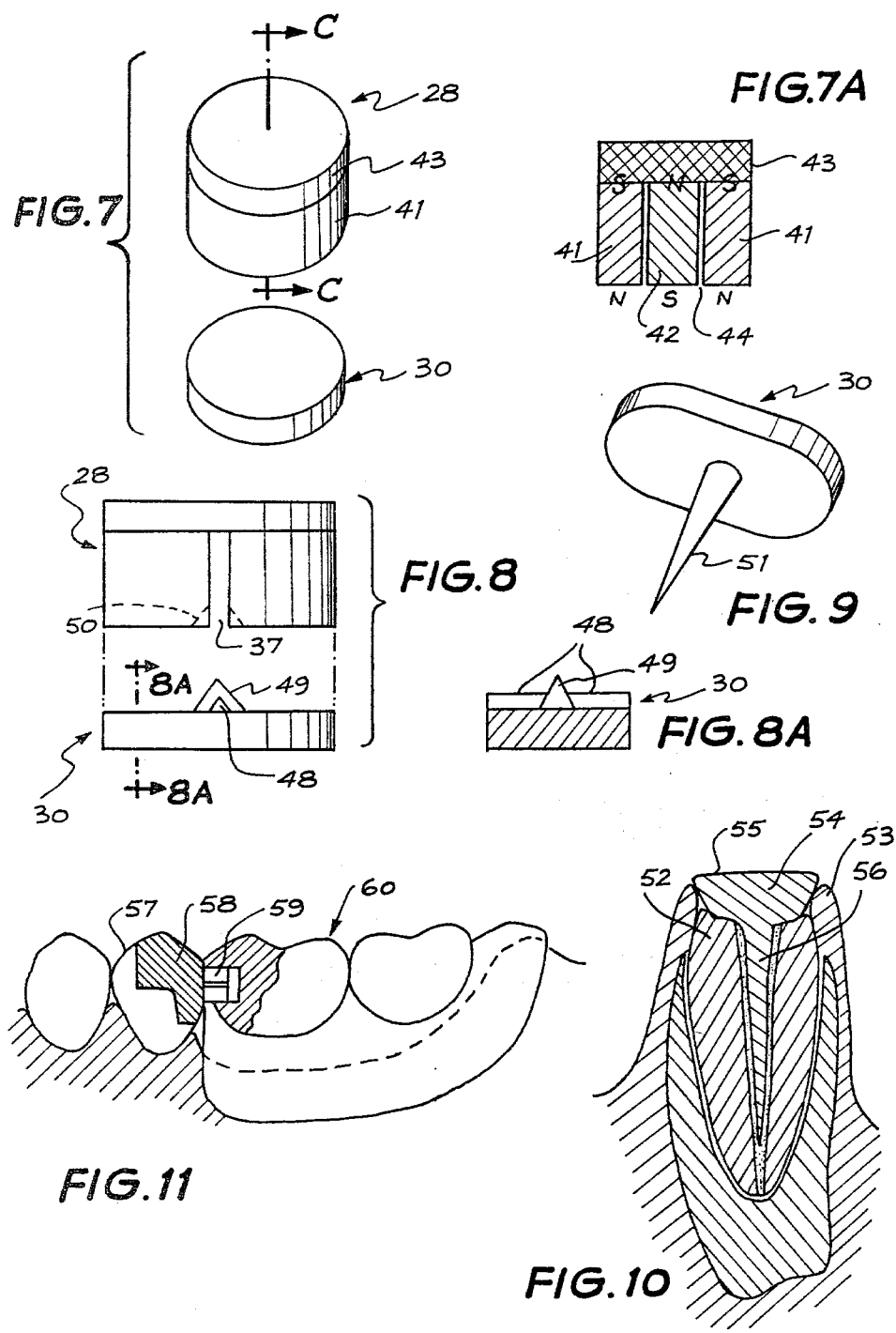

DENTURE RETENTION

FIELD OF THE INVENTION

This invention relates to prosthetic dentistry and is more specifically concerned with anchorage of artificial dentures by use of magnet elements.

BACKGROUND OF THE INVENTION

If a person is entirely without teeth an artificial denture which replaces the missing teeth is said to be "complete", and an artificial denture which replaces the missing teeth of a person possessing some natural teeth is said to be "partial". At the present time, the preferred way of retaining a complete denture is through the suction provided by a peripheral seal of the denture borders with the soft gum tissues, and by the adhesion provided by a saliva film at the interface of the denture and tissue. The preferred way of retaining a partial denture is to employ flexible metal arm-type retainers or clasps which are attached to the denture and engage natural or contrived undercuts which are present on one or more of the remaining natural teeth, or by the use of one or more so-called precision attachments. Such precision attachments consist of two interlocking components, one of which is attached to the denture and the other to a natural tooth.

Partial dentures require skill and care in design, construction and fitting to prevent damage to and possible loss of the remaining natural teeth. The flexible metal arm-type retainers are simpler and less expensive but are less satisfactory in service than the precision attachment retainers. The precision attachment retainers require more complicated clinical and laboratory procedures during denture construction and more care in service and cleaning than the flexible metal arm-type retainers.

Complete dentures are simple to construct but provide little retention, especially in the case of the lower jaw, and the retention available initially may decrease with age because resorbtion of the bony ridges and tissue changes often occur. In addition, the tissues covering the bony ridges are required to absorb the force of chewing, and are thus subject to irritation and trauma. One way of avoiding this trauma is to implant at least one metal, ceramic or plastic material post in the jawbone and to construct the denture using the post(s) for support. This method requires extensive surgical and operative skills.

A variation of this technique involves root filling, decoronating and trimming flush with the gingival margin teeth which would otherwise be extracted, and using the resultant stumps in the same way as implanted posts, either alone or in combination with precision attachments. The first of these procedures provides a so-called overlay denture, and the support provided by the tooth stumps relieves the gums of much of the chewing force, but does not provide retention as such. The second of the two procedures provides a so-called removable precision overlay denture which provides both support and retention, but the tooth stumps used for this purpose are subjected to abnormally high forces during chewing.

The present invention, as hereinafter defined, seeks to avoid the problems associated with self-retained dentures and the use of flexible metal arm or precision attachments by using magnet elements for retaining the dentures in position.

DESCRIPTION OF PRIOR ART

The use of magnets in dentistry is not new. The mutual attraction of paired magnets of various types has been used with some success as a retention aid for maxillofacial prostheses and obturators, and for complete dentures. An article published by S. J. Behrman in the Journal of Prosthetic Dentistry, Vol. 10: 807–841 (September-October) 1960 and entitled "The Implantation of Magnets In The Jaw To Aid Denture Retention" discloses the implantation of Teflon (reg'd T. M.) coated cobalt-platinum bar magnets in the bone of the mandible, for the purpose of retaining mandibular complete dentures containing similar but oppositely poled magnets. Behrman claims complete safety, no adverse physiological effects, excellent gross and microscopic tissue findings, favourable bone response, enhanced denture retention and encouraging patient reaction if 450 cases. However, there are two particularly significant features which should be noted in respect of the approach taken by Behrman. Firstly, the magnet element implanted in the bone of the mandible is located below the mucoperiosteum (i.e. away from contact with the magnet in the denture) and, secondly, two separate magnets are employed. The use of two, separated, magnets provides for a magnetic field through the mucoperiosteum between the magnets and a loop-closing field through other bone and tissue of the implantee.

Apart from possible physiological rejection of the implanted magnet proposed by Behrman, it is thought that mutual attraction effects between the separated magnet elements could lead to difficulties. In this regard, reference is made to a publication by P. D. Toto, N. C. Choukas and D. D. Sanders in J. Dent. Res., Vol. 41: 1438–1449 (November-December) 1962. This publication teaches that uncoated cobalt-platinum magnets which were implanted in the mandibles of dogs would not remain in place when exposed to the attraction of opposite poled magnets splinted into position over the mucosa, although isolated magnets were well tolerated by bone and overlying mucoperiosteum.

SUMMARY OF PRESENT INVENTION

The present invention seeks to avoid, or at least reduce, the above discussed problems of denture retention by providing a method of retaining either complete or partial dentures in place. The method comprises mounting a first element to at least one support associated with a person's jawbone, the first magnet element being exposed at or above the gingival margin of the person's gum, and locating at least one second magnet element in a denture to be worn by the person. Each second magnet element is located to align with and to abut a respective first magnet element when the denture is fitted to the person. It is emphasized that the first and second magnet elements are arranged and located to abut, and to be attractive to one another, when the denture is fitted to the wearer.

The present invention further provides a method of fitting a denture to a patient and which comprises the steps of mounting a first magnet element to at least one support associated with the patient's jawbone such that such magnet element is exposed at or above the gingival margin of the patient's gum, forming a denture to suit the patient, and locating at least one second magnet element in the denture in a manner such that it or they will align with and abut the first magnet element(s) when the denture is fitted to the patient.

The present invention still further provides a denture per se of the type above defined, and a magnet element per se for use in the denture.

Both the first and the second magnet elements may be constituted by magnets as such. Alternatively, one or other (but not both) of said first and second magnet elements may be constituted by a magnetizable element. Such magnetizable element is defined as one that displays significant magnetic properties only when influenced by a magnetic field.

PREFERRED FEATURES OF PRESENT INVENTION

Preferbly, the first magnet element comprises a ferromagnetic element, and the second magnet element, which is located within the denture, preferably comprises a cobalt-rare-earth magnet.

In the interest of avoiding or militating against possible adverse biological effects of leakage flux from an open-loop magnet system, the first and second magnet elements are preferably arranged and constructed to form a closed loop system. This may be achieved by using a U-shaped magnet structue for both elements, one of the structures being inverted with respect to the other both geometrically and in terms of polarity. Most preferably, the closed loop arrangement is achieved by using a U-shaped magnet structure for one of the magnet elements and a keeper of ferromagnetic material for the other magnet element, the keeper being shaped and sized to bridge the two poles of the magnet element.

The support for the first magnet element is preferably constituted by a natural tooth which, if beyond repair, is root filled, decoronated, trimmed flush with the gingival margin and fitted with the magnet element. Such element may be held in place by an adhesive only, or it may be pinned and adhered into place.

If the method of the present invention is to be applied to a person who previously has had all teeth completely removed, the support for the first magnet element may be constituted by a dental implant which is fitted with the magnet element and which locates such element at or above the gingival margin for contact with the (second) magnet element in the denture.

Each pair of first and second magnet elements need not necessarily be arrayed or aligned in a vertical direction. If, for example, a partial denture is required to supplement existing natural teeth, one or more of the existing teeth may be capped, crowned or filled with a ferromagnetic material to, in effect, present a said first magnet element at the side of such tooth or teeth. Then, the second magnet element would be located within the denture such that its poles align with the material. Such arrangement provides predominantly for lateral support for the denture. However, a component of support in a vertical direction will also exist, but if this is found to be insufficient for acceptable denture retention, a mechanical keying arrangement may be structured between the existing teeth and the denture to provide for greater vertical retention.

Retention may be achieved according to the present invention by the use of a single said first magnet element and a single said second magnet element only, particularly when a partial denture is to be retained. However, particularly in the case of retention of a complete denture, spaced apart pairs of elements are preferably employed. For example, a complete overlay denture may be retained by locating said first magnet elements in the left and right hand side canine teeth and by locating two correspondingly placed second magnet elements in the denture.

Preferably, the first magnet element and the second magnet element are provided with geometrical locating projections and recesses repectively, to facilitate correct alignment of the denture during and after initial fitting.

When an existing tooth to which the first magnet element is to be fitted is suspect, the tooth may be fitted with an endodontic stabilizer and the magnet element be fitted either directly or indirectly to the stabilizer.

Also, when fitting the magnet element or elements to a denture, during the manufacture of such denture, a flexible mounting may be provided for the or each magnet element. Such flexible mounting may be formed by a resilient type of cement or by location of a resilient device such as a compression spring behind the magnet element within the denture.

In order to accommodate age induced movement of the support for the first magnet element and to ensure sustained accurate registration of such element with the second magnet element, the magnet element may be adhered into a pocket within the denture by use of a semi-pliable adhesive.

The denture retention system of the present invention as hereinbefore considered is applicable to both the upper and/or the lower jaw of a patient.

The invention is further described in the context of exemplary embodiments thereof and with reference to the accompanying drawings.

DESCRIPTION OF DRAWINGS:

In the drawings:

FIG. 5 shows an enlarged view of a first type of magnet and keeper arrangement for use in the denture retention system as shown in FIG. 4, FIG. 5A shows a section of the magnet of FIG. 5 as viewed in the direction plane A—A, FIG. 6 shows an enlarged view of a second type of magnet and keeper arrangement for use in the denture retention system as shown in FIG. 4, FIG. 6A shows a section of the magnet of FIG. 6 as viewed in the direction of section B—B, FIG. 7 shows an enlarged view of a third type of magnet and keeper arrangement for use in the denture retention system as shown in FIG. 4, FIG. 7A shows a section of the magnet of FIG. 7 as viewed in the direction of section plane C—C, FIG. 8 shows a modified form of the magnet and keeper arrangement of FIG. 6, FIG. 9 shows a modified form of the keeper of FIG. 6, FIG. 10 shows a scrap view of a keeper mounted to a tooth stump, the keeper enlarging the effective contact, surface area of the stump, and FIG. 11 shows a scrap view of a natural tooth and a portion of a partial denture retained by the tooth.

DETAILED DESCRIPTION OF EMBODIMENTS OF THE INVENTION

Figure 1:
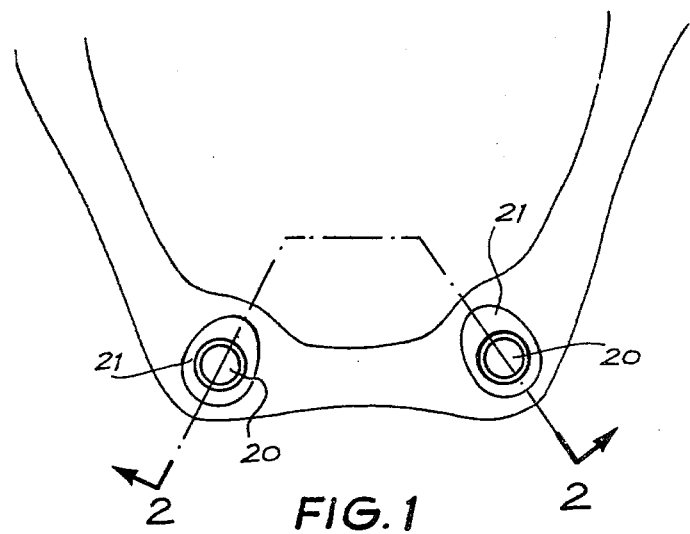
FIG. 1 is a diagrammatic illustration of the lower jaw of a patient in which two canine tooth stumps are shown fitted with a magnetizable element.
Figure 2:
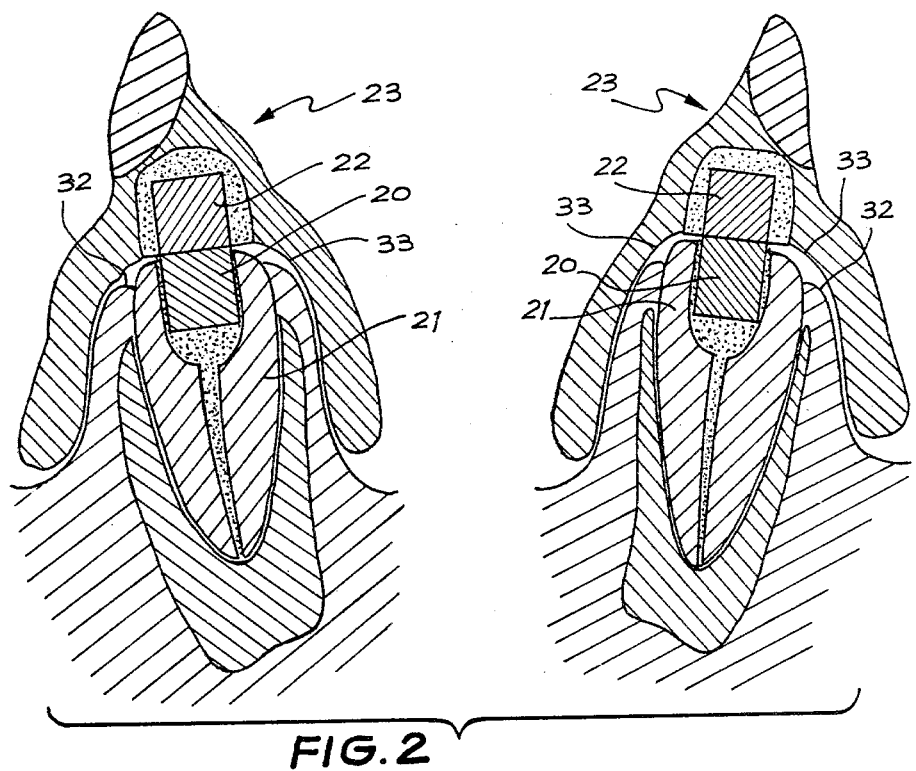
FIG. 2 shows a section through the patient's jaw, the section being taken along the lines 2—2 of FIG. 1, with a denture being shown overlaying the jaw section and retained in place by magnet arrangements.

The denture retention system as shown in FIGS. 1 and 2 of the drawings incorporates four magnet elements, two of which are designated by numeral 20 and located within supports constituted by tooth stumps 21. The remaining two magnet elements, designated by numeral 22, are located within the body of an overlay denture 23 and are orientated for pole attraction to the elements 20.

Each of the magnets 20 and 22 is in the form of a solid cylinder which has oppositely poled end faces and, therefore, the magnet elements do not themselves form a complete magnetic circuit, there being an unbounded magnetic flux circuit through the patient's bone and tissue to link the remote ends of each pair of magnet elements. This arrangement is referred to herein as an open loop system and whilst such a system may be proved to be biologically and physiologically acceptable, the applicant prefers the use of a closed loop system which provides for a minimal leakage flux.

Figure 3:
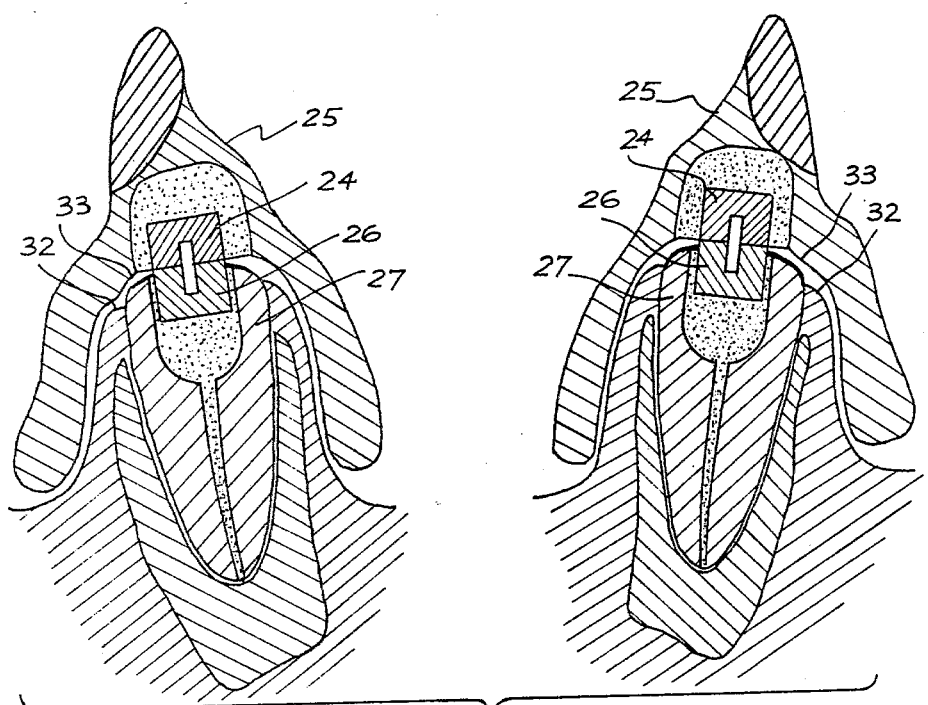
FIG. 3 shows the same section as FIG. 2 but with a different magnet arrangement being illustrated.

A typical closed loop system which uses paired magnet elements is shown in FIG. 3. In this case two inverted U-shaped magnet elements 24 are located within the overlay denture 25 and another two U-shaped magnets 26 are located within tooth stumps 27 within the patient's mouth. The elements 24 are orientated with respect to the abutting elements 26 for polar attraction.

Figure 4:
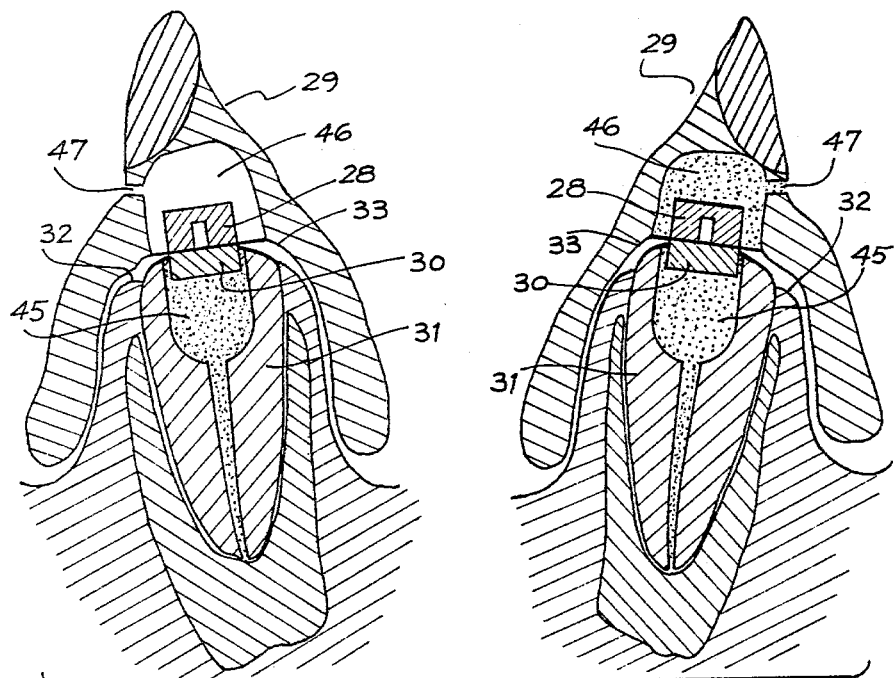
FIG. 4 shows the same section as FIG. 2 but with a further magnet arrangement being illustrated and with the respective magnet arrangements being shown in different assembly stages.

Another, more preferred closed loop system is shown in FIG. 4 of the drawings, this comprising two inverted U-shaped magnet elements 28 which are located within an overlay denture 29, and two magnetizable material keeper elements 30 which are located within respective tooth stumps 31.

A feature which links the embodiments shown in FIGS. 2 to 4 of the drawings and which is essential to the present invention is the absence of tissue between the elements 20, 22, elements 24, 26 and elements 28, 30. Thus, the elements 20, 26 and 30 are located within their supports so as to be exposed adjacent the gingival margin 32 of the patient's gum, and the magnet elements 22, 24 and 28 are located with their respective face(s) exposed at the tissue-fitting surface 33 of the overlay denture, whereby the elements of each pair may abut one another when the denture is fitted to the patient.

In the interest of gaining maximum efficiency from the magnet elements and having regard to the high reluctance of any airgap between confronting poles (or poles and keeper), it is most desirable that the paired elements actually abut one another. However, this condition may not be achievable under all conditions and an airgap of up to, say, 500 micrometers may be tolerated. For all practical pruposes this may be regarded as constituting "abutting" contact between the elements and such term as used herein shall be construed to include either physical contact or close juxtaposition.

The magnet elements 28 and the keepers 30 as shown in FIG. 4 may take any one of the configurations exemplified by FIGS. 5 to 7.

As shown in FIGS. 5 and 5A the magnet element 28 comprises two semi-cylindrical magnet portions 34 and 35 which are inverted with respect to one another so as to be oppositely poled and connected by an integral bridging strap 36. The two magnet portions each have a semi-circular cross-section as shown in FIG. 5A and they are spaced apart by an airgap 37. The keeper 30 has a profile corresponding to that of the magnet element cross-section.

The magnet element 28 as shown in FIGS. 6 and 6A is similar to that shown in FIG. 5, but it comprises two magnet portions 38 and 39 each of which is profiled as a major segment of a circle. The two magnet portions 38 and 39 are inverted with respect to one another, so as to be oppositely poled, and are connected by an integral bridging strap 40. In this case the keeper 30 is profiled to correspond approximately with the cross-sectional profile of the element 28.

The magnet element 28 as shown in FIGS. 7 and 7A is different from the others shown, in that it has an outer toroidal form portion 41 and an inner cylindrical portion 42. The two portions 41 and 42 are inverted with respect to one another, so as to present opposite poles at their respective ends, and the two portions are bridged by a disc-shaped integral cap 43. An annular airgap 44 separates the two portions, and the cross-sectional area of the pole face of the magnet portion 41 is preferably equal to that of the pole face of magnet portion 42. The keeper 30 has a circular profile and has a diameter approximately equal to that of the toroidal portion 41.

The magnet elements 20, 22, 24, 26 and 28 are preferably formed from a cobalt-rare-earth material, cobalt-samarium being most preferred. The keeper element 30 is preferably formed from a ferromagnetic stainless steel, and it may be either cast or stamped to achieve the desired configuration.

The exposed pole surfaces of the magnet elements and/or the magnet keeper elements may be capped with a thin stainless steel or platinised gold shim-metal having a thickness in the order of 5 to 10 microns. Such capping may be found necessary in certain circumstances to prevent corrosion and/or to inhibit possible toxic effects, but it is thought that in most circumstances the cap should not be necessary.

One procedure which may be used for fitting the magnets and keepers to a patient is now described with reference to FIG. 4. The patient's two mandibular canine teeth 31 are root-filled, decoronated trimmed approximately flush with the gingival margin 32, and formed with a cavity 45. The keeper elements 30 are then cemented into the cavities 45 and the magnet elements 28 are fitted onto and aligned with the respective keeper elements.

An impression is then taken from the patient with the magnet elements 28 in place, the magnet elements are removed from the impression for later use in the denture, and a cast is prepared from the impression. An overlay denture 29 is then constructed for the patient using the cast, the holes left by the magnet elements which were removed from the impression being preserved in the denture base and therafter being enlarged slightly to form cavities 46. The magnet elements 28 are then reseated on the keeper elements 30 in the patient, as at the commencement of the procedure, and the denture 29 is then positioned in the patient's mouth and over the magnet elements. A cold-curing acrylic resin is then injected into the denture base, by way of pre-drilled apertures 47, to surround and secure the magnet elements 28. After curing of the resin, the denture (including the magnet elements 28) is removed and any excess resin is trimmed from the tissue-forming surface 33 of the denture.

As an alternative procedure, a form of the well-known "transfer coping technique" may be employed for fabricating the overlay denture, such technique being modified to use the magnet element 28 as the coping.

To ensure accurate reseating of the denture to the keeper elements 30, such keeper elements may be formed with geometrical locating projections 48 and 49, as shown in FIG. 8. The projection 48 is preferably positioned to align and locate in the airgap groove 37 of the magnet element 28, and the projection 49 locates within a dimple 50 formed in the magnet element.

To assist in location and retention of the keeper element 30, and to impart greater structural rigidity to a tooth which is used to support the keeper, the keeper element may be constructed as shown in FIG. 9 to include a spigot 51. In use, the spigot 51 is located within an enlarged nerve canal of the supporting tooth.

The keeper element 30 need not necessarily be located entirely within the tooth stub 31. Thus, when using a tooth which has a small cross-section to support the keeper element, a technique as shown in FIG. 10 may be employed. In this case the tooth 52 is decoronated to a level below the gingival margin 53 and a keeper element 54 is cemented into place in the tooth stump. The keeper element has divergent side walls to provide a pole face 55 which has a cross-sectional area greater than that available in the tooth. To permit mounting of the keeper element to the tooth it is provided with a spigot portion 56 in the same manner as the element shown in FIG. 9.

Although the denture retention system described thus far has involved vertically aligned magnet and keeper elements, it will be understood that the invention may be applied with benefit to lateral retention of dentures, particularly in the case of partial dentures. One typical arrangement is shown in FIG. 11 of the drawings wherein a natural tooth having a decayed crown but a sound root structure is used to retain an adjacent partial plate. The drawing is very diagrammatic but it shows an existing tooth which is partially crowned with a ferromagnetic stainless steel cast insert 58. The insert is structured so as to form one side of the tooth 57 and to act as a magnetizable keeper for a laterally projecting magnet element 59. The magnet element 59 is located on it side and is positioned within one side wall of a partial denture 60.

The invention as described herein may be employed not only in cases where a person has tooth roots available for supporting the magnetizable elements or keepers, but also in the case of a person being edentate. Under such circumstance, support for the retaining magnet or keeper element may be provided by a dental implant, the implant being used in the manner of but in lieu of the tooth stump 31 as shown in FIG. 4 of the drawings.

The expression "denture" as used in the preceding description and in the following claims is intended to embrace any and all artificial substitutes for one or more missing natural teeth.

I claim:

1. A method of retaining a denture in place, the method comprising:
    mounting a first magnet element to a support associated with a person's jawbone, the first magnet element having a generally horizontal surface portion thereof exposed adjacent the gingival margin of the person's gum,
    locating a second magnet element in a denture to be worn by the person, the second magnet element having a generally horizontal surface portion thereof exposed to contact the exposed surface portion of the first magnet element when the denture is fitted to the person and the surface portions of the two magnet elements being magnetically attractive, and
    locating the denture in the person's mouth in a position such that the second magnet element is located to align substantially vertically with the first magnet element and such that said surface portions of the first and second magnet elements abut when the denture is fitted to the person.

2. The method as claimed in claim 1, wherein both the first and second magnet elements comprise magnets that exhibit a magnetic field.

3. The method as claimed in claim 1, wherein one of the first and second magnet elements comprises a magnet that exhibits a magnetic field and the other of the first and second magnet elements comprises a magnetizable element which is formed from a ferromagnetic material.

4. The method as claimed in claim 3, wherein the second magnet element is that which is constituted by the magnet that exhibits a magnetic field.

5. The method as claimed in claim 1, wherein the first and second magnet elements co-operate to form a closed magnetic circuit when in abutting contact.

6. A method of retaining a denture in place, the method comprising:
    mounting to a support associated with a person's jawbone a first magnet element, in the form of a magnetisable keeper element, in such a manner as to expose a generally horizontal surface portion thereof adjacent the gingival margin of the person's gum,
    locating in a denture to be worn by the person, a second magnet element in the form of a U-shaped magnet, having spaced-apart pole faces disposed substantially in a horizontal plane, while exposing the pole faces to enable contact with the exposed surface portion of the first magnet element and to form a closed magnetic circuit therewith when the denture is fitted to the person, and
    locating the denture in the person's mouth in a position where the second magnet element is aligned substantially vertically with the first magnet element and such that the pole faces of the second magnet element abut the exposed surface portion of the first magnet element when the denture is fitted to the person.

7. The method as claimed in claim 6, wherein there are at least two supports, each of which mounts a said first magnet element, and wherein there are at least two said second magnet elements located in the denture, respective said first and second magnet elements being paired.

8. The method as claimed in claim 6, wherein the second magnet element comprises a cobalt-rare-earth magnet.

9. The method as claimed in claim 6 including the step of providing the first and second magnet elements with geometrical locating projections and recesses respectively, thereby facilitating correct alignment of the denture during and after initial fitting.

10. The method as claimed in claim 6 including the step of forming the keeper with a spigot arranged to be located within an aperture formed within the support.

11. The method as claimed in claim 6 wherein the step of locating the second magnet element includes locating the second magnet element in the denture in a manner which provides for a small degree of movement of the second magnet element relative to the denture.

12. The method as claimed in claim 6 including the prior steps of decoronating the root of a tooth associated with the person's jawbone, filling the root, and forming the root with a cavity to receive the first magnet element.

13. The method as claimed in claim 6 including the prior step of providing a dental implant to serve as the support associated with the person's jawbone.

14. A method of fitting a denture to a patient and which comprises the steps of:
mounting to a support associated with the patient's jawbone, a first magnet element in the form of a magnetisable keeper having a geneally horizontal surface portion thereof exposed adjacent the gingival margin of the patient's gum,
forming a denture to suit the patient,
locating in the denture a second magnet element in the form of a U-shaped magnet having spaced-apart pole faces disposed in a substantially horizontal plane and exposed to contact the exposed surface portion of the first magnet element and to form a closed magnetic circuit therewith when the denture is fitted to the patient, and
locating the denture in the patient's mouth in a position where the second magnet element is aligned substantially vertically with the first magnet element and the pole faces of the second magnet element abut the exposed surface portion of the first magnet element.

15. The method as claimed in claim 12 including the steps of
mounting a said first magnet element to each of at least two said supports associated with the patient's jawbone, and
locating at least two said second magnet elements in the denture where each said second magnet element is aligned substantially vertically with a said first magnet element when the denture is fitted to the patient.

16. The method as claimed in claim 13 including the steps of
forming a support by decoronatling and root filling a natural tooth and forming a cavity therein for receiving the first magnet element, and
mounting a first magnet element to said support.

17. A denture comprising
a base having a gum tissue conforming surface,
artificial teeth mounted to the base, and
at least one magnet element located in the base,
the magnet element comprising a U-shaped magnet having spaced-apart pole faces, the pole faces being disposed in a common plane and being both exposed at the gum tissue conforming surface of the base,
the pole faces of the magnet element having a total effective area not greater than the cross-sectional area of a single decoronated tooth with which the magnet aligns when the denture is fitted to a wearer.

18. A dental fitting, comprising
a first magnet element mounted on a support associated with one member of a person's jawbone and having a generally horizontal surface portion exposed adjacent the gingival margin of the person's gum,
a second magnet element in a denture worn by the person on the same member of the jawbone and facing said first magnet element, said second magnet element having a generally horizontal surface portion exposed to and in contact with the surface portion of the first magnet element.

* * * * *